United States Patent
Brown et al.

(10) Patent No.: US 6,743,587 B2
(45) Date of Patent: Jun. 1, 2004

(54) ACE GENOTYPE WHICH CORRELATES WITH IMPROVED SUCCESS IN SODIUM EXCRETION IN HYPERTENSIVES WITH EXERCISE

(75) Inventors: Michael Brown, Laurel, MD (US); James Hagberg, Columbia, MD (US); Robert Ferrell, Pittsburgh, PA (US)

(73) Assignees: University of Maryland, College Park, MD (US); University of Pittsburgh, Pittsburgh, PA (US)

( * ) Notice: Subject to any disclaimer, the term of this patent is extended or adjusted under 35 U.S.C. 154(b) by 11 days.

(21) Appl. No.: 09/986,989

(22) Filed: Nov. 13, 2001

(65) Prior Publication Data

US 2002/0098502 A1 Jul. 25, 2002

Related U.S. Application Data

(60) Provisional application No. 60/247,951, filed on Nov. 13, 2000.

(51) Int. Cl.[7] .......................... C12Q 1/68; C12P 19/34; C07H 21/04
(52) U.S. Cl. .......................... 435/6; 435/91.2; 536/23.2; 536/23.5
(58) Field of Search .................. 435/6, 91.2; 536/23.2, 536/23.5

(56) References Cited

U.S. PATENT DOCUMENTS 6,399,306 B1 * 6/2002 Hagberg et al. ................ 435/6

FOREIGN PATENT DOCUMENTS

WO    WO 99/45383 A1 * 9/1999

OTHER PUBLICATIONS

Donoghue, M. et al. A novel angiotensin–converting enzyme–related carboxypeptidase (ACE2) converts angiotensin I to angiotensin 1–9. Circulation Research 87(5):e1–e9 (Sep. 2000).*

Kingwell, B.A. et al. Effects of walking and other exercise programs upon blood pressure in normal subjects. Medical Journal of Australia 158(4):234–238 (Feb. 1993).*

Hagberg, J.M. et al. Effect of exercise training in 60– to 69–year–old persons with essential hypertension. American Journal of Cardiology 64(5):348–353 (Aug. 1989).*

Urata, H. et al. Antihypertensive and volume–depleting effects of mild exercise on essential hypertension. Hypertension 9(3):245–252 (Mar. 1987).*

Brown, et al., "Improvement of Insulin Sensitivity by Short–term Exercise Training in Hypertensive African American Women", Hypertension, vol. 30, No. 6, pp. 1549–1553 Dec. 1997.

* cited by examiner

*Primary Examiner*—Diana B. Johannsen
(74) *Attorney, Agent, or Firm*—Arent Fox PLLC

(57) ABSTRACT

A method of increasing sodium excretion levels in a hypertensive subject by identifying a subject having an II genotype for an angiotensin converting enzyme gene, and engaging the subject in limited exercise training for a period of time sufficient to increase the subject's sodium excretion levels.

1 Claim, 2 Drawing Sheets

ACE GENOTYPE WHICH CORRELATES WITH IMPROVED SUCCESS IN SODIUM EXCRETION IN HYPERTENSIVES WITH EXERCISE

This nonprovisional application claims the benefit of U.S. Provisional Application No. 60/247,951, filed Nov. 13, 2000.

FIELD OF THE INVENTION

The present invention relates to identifying an ACE genotype which correlate with improved success in sodium excretion in hypertensive individuals engaged in exercise training.

BACKGROUND OF THE INVENTION

Regular endurance exercise has been shown to lower blood pressure in hypertensive patients (see, e.g., Hagberg et al., *J. Cardiov. Risk*, vol. 2, pp. 296 et seq., 1995) and is widely recommended as an initial non-pharmacological treatment. One of the potential mechanisms underlying this effect of exercise training is an increase in sodium excretion. Unfortunately, some individuals, no matter how rigorously they exercise, are unable to improve their conditions, while others benefit to a much greater extent than predicted. These results underscore the fact that many factors contribute to an individual's well-being. Such factors include, for example, behaviors such as diet and exercise, genetic makeup, and environment. While behavior and environment can be controlled, altered or regulated, an individual's genetic makeup is essentially predetermined and set at birth.

Angiotensin converting enzyme (ACE) is the enzyme responsible for catalyzing the conversion of angiotensin I, a relatively inactive tissue and plasma vasopressor hormone, into the potent and highly active vasopressor hormone angiotensin II. This cascade of reactions is part of the renin-angiotensin-aldosterone system that has long been known to be an important regulator of arteriolar relaxation and vasoconstriction, and hence blood pressure, in humans and animals. The ACE gene is polymorphic with two common alleles designated "I" and "D", resulting in three genotypes: "II", "ID" and "DD". The "D" allele has a 287-base pair marker in intron 16 of the ACE gene deleted, whereas the "I" allele has the 287-base pair marker inserted. The "D" allele is associated with increased levels of ACE in both plasma and ventricular tissues. Increased levels of ACE contributes to increased myocardial and vascular smooth muscle growth and increased arteriolar vasoconstriction. Thus, the presence of the "D" allele is hypothesized to have deleterious effects on the cardiovascular system, and, in fact, the "D" allele has been associated with increased risk of left ventricular hypertrophy, cardiovascular disease, and sudden cardiovascular death. Prior studies have sought to determine if an association exists between ACE "DD" genotype and blood pressure regulation. Results from human studies have been mixed, with most studies unable to identify an association between ACE gene variants and blood pressure in Caucasian and African Americans. (Schunkert et al., *Hypertension*, vol.29, pp. 628 et seq., 1997; Rotimi et al., *Hypertension*, vol. 24, pp. 591 et seq., 1994.) However, one study found an association between hypertension and the "D" allele in African Americans. (Duru et al. *Am. J. Hypertension*, vol. 7, pp. 759 et seq., 1994.)

Published PCT application WO 99/45383 (Hagberg et al.) discloses that hypertensive individuals with different ACE genotypes exhibited different degrees of success in reducing their blood pressure levels through exercise. The results were dependent on the duration of the exercise protocol. The inventors found that those individuals having an "II" or "ID" genotype exhibited more reduction in blood pressure levels than those with a "DD" genotype, after the long-term exercise protocol. However, after the most short-term exercise protocol, those subjects having "II" or "DD" genotypes exhibited more reduction in blood pressure levels than those with "ID" genotypes. After a limited exercise protocol that was more extensive than the short-term exercise protocol, those subjects having an "II" genotype exhibit more reduction in blood pressure levels than those with "ID" or "DD" genotypes.

In a separate study, it was reported that sodium excretion rate in African American hypertensive women increased 37% after 7 days of exercise. (Brown et al., *Hypertension*, vol. 30, pp. 1549 et seq., 1997.) However, no genotyping was reported in this study, and thus there was no identification with respect to whether those individuals with a certain genotype derived more benefit from the exercise. An object of the present invention is to identify those hypertensive individuals who are more likely to benefit from exercise in increasing sodium excretion, based on their genotype.

SUMMARY OF THE INVENTION

The present inventors have discovered that the angiotensin converting enzyme (ACE) gene serves as a genetic marker which positively correlates with improved success in increasing sodium excretion levels in hypertensive individuals. Specifically, the inventors have found that those individuals possessing the "II" ACE genotype increased their sodium excretion levels significantly more than those individuals possessing either the "ID" or "DD" ACE genotype. The present invention is directed to a method of increasing sodium excretion levels in a hypertensive subject, comprising:

identifying a hypertensive subject having an II genotype for an angiotensin converting enzyme gene; and engaging the subject in limited exercise training for a period of time sufficient to increase the subject's sodium excretion levels.

DETAILED DESCRIPTION OF THE INVENTION

Figure 1:
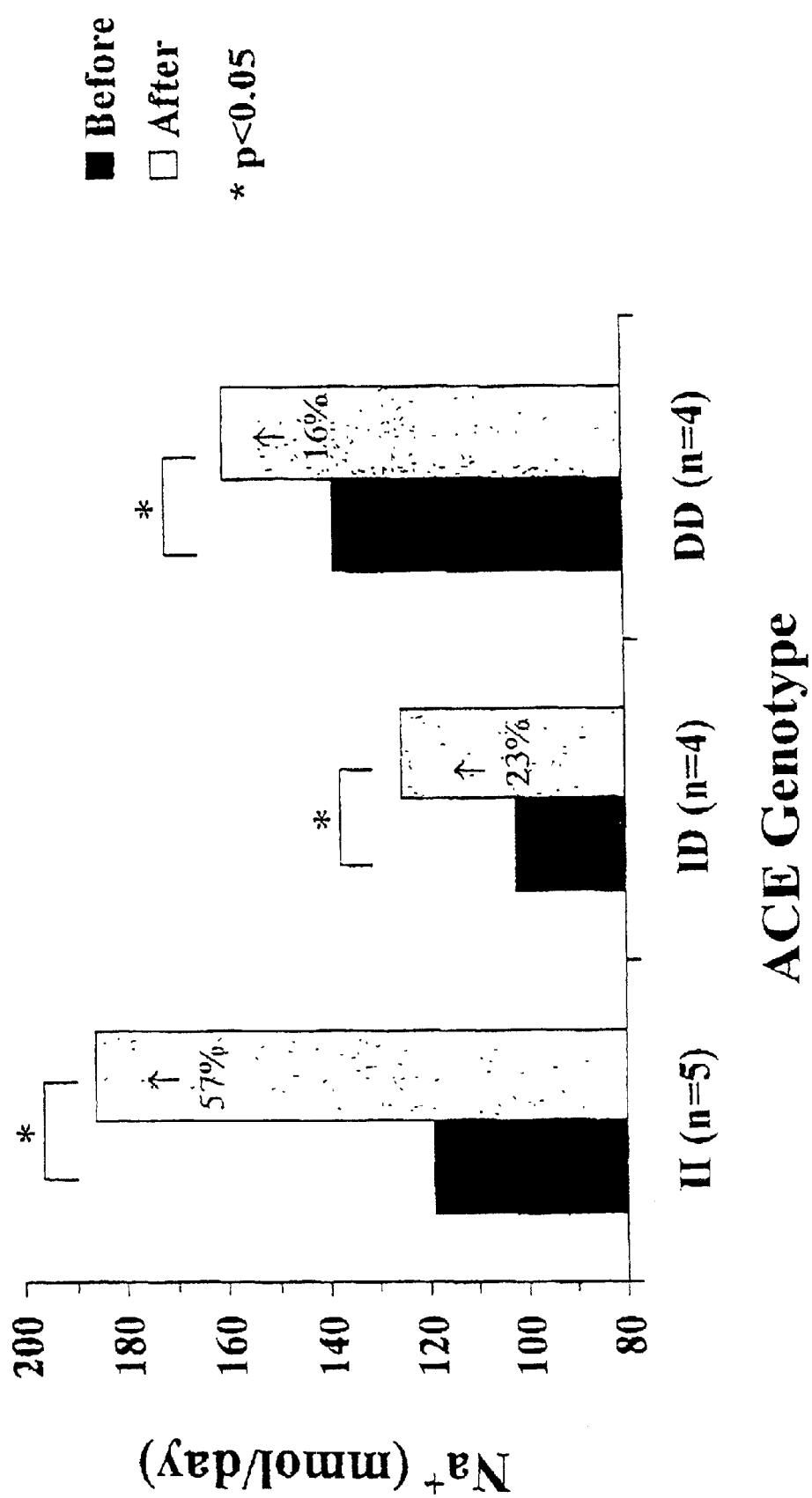
FIG. 1 shows the sodium excretion levels of thirteen subjects, grouped by ACE genotype, before and after limited exercise training.

The inventors have found that the ACE genetic marker positively correlates with improved success in increasing sodium excretion levels in hypertensive individuals, such that those individuals having an II genotype have improved success as compared with other genetic makeup at the same gene locus.

Sodium excretion may be measured in body fluids such as urine, sweat, saliva or blood. After establishing baseline levels, in order to determine the change in sodium excretion levels, sample collection can occur at any time period before or after a single course of exercise. However, it is preferred that sample collection be conducted 0–24 hours after a single course of exercise, most preferably about 14–18 hours after a single course of exercise.

The term "single course of exercise", as used throughout this application, means a cardiovascular exercise session of any type which is conducted during one day. An exercise session may comprise an aerobics class, treadmill training, step machine, cycling, or any other suitable cardiovascular exercise regimen. For most cases, exercise may be completed in, for example, 30 minutes to 3 hours, preferably between 45 minutes and 90 minutes, with optional brief rest periods of 3–15 minutes, however this amount would vary depending on the health and endurance of the subject. It is preferred that the exercise regimen be selected to ensure that each subject's exercise heart rate corresponds to between 50 and 80%, most preferably about 65%, of their heart rate reserve.

The term "limited exercise" means about 5–9 single courses of exercise, preferably about 6–8, or 7 single courses of exercise, over the exercise period. The exercise period in the case of a limited exercise protocol is preferably about 5–30 days, more preferred about 5–20 days, most preferred about 5–12 days. The exercise period can also be a daily single course of exercise (i.e., daily exercise for about 5–9 days, depending on the number of single courses of exercise in the protocol).

The time between exercise periods may be from 2–60 days or more. The term "between exercise periods" means that time during which the subject is not in a limited exercise program.

The present inventors have discovered that hypertensive individuals with different ACE genotypes exhibit different degrees of success in increasing their sodium excretion levels through exercise. These results could not have been predicted from initial patient screening.

The inventors have found that those individuals having "II" genotype exhibit more increase in sodium excretion levels than those with "ID" or "DD" genotypes, after limited exercise.

EXAMPLES

Example 1

Variations in Increase of Sodium Excretion in Thirteen (13) Subjects After Limited Exercise Thirteen subjects aged 51±8 years were obese (body fat>35%), sedentary (VO$_2$max 21.8±4.8 ml/kg/min), hypertensive (BP 143±3 over 91±2 mmHg) male and female African Americans. The insertion/deletion ACE gene ("II" n=5; "ID" n=4; "DD" n=4) polymorphism was determined using standard PCR procedures.

Exercise consisted of seven (7) consecutive days of treadmill walking and stationary cycling for 50 min/d at 65% of heart rate reserve. Sodium excretion was determined by 24-hour urine collection at baseline, and beginning 14–18 hours after the last exercise session. Subjects consumed diets identical in macronutrient and sodium content during the testing periods. Baseline sodium excretion, fasting insulin and glucose levels, percent body fat, VO$_2$max and casual mean blood pressure (MBP) were similar in the ACE genotype groups, as shown in Table 1 below:

TABLE 1

| | ACE Genotype | | |
|---|---|---|---|
| Variable | II (n = 5) | ID (n = 4) | DD (n = 4) |
| Age (yrs) | 51 ± 6 | 56 ± 9 | 45 ± 5 |
| Body Fat (%) | 42.4 ± 13.4 | 39.2 ± 2.9 | 44.8 ± 2.0 |
| VO$_2$max (ml/kg/min) | 22.5 ± 6.6 | 24.2 ± 3.7 | 19.9 ± 2.0 |
| MBP (mmHg) | 110.3 ± 2.4 | 108.1 ± 1.8 | 113.2 ± 3.5 |
| Fasting Insulin (uU/ml) | 8.4 ± 2.3 | 9.8 ± 5.1 | 11.8 ± 5.0 |
| Urinary Sodium (mmol/d) | 119 ± 26 | 102 ± 16 | 138 ± 11 |

Values are expressed as mean ± SD

After seven days of exercise training, sodium excretion was significantly increased in all three genotype groups, as shown in Table 2 below:

TABLE 2

| | ACE Genotype | | |
|---|---|---|---|
| Variable | II (n = 5) | ID (n = 4) | DD (n = 4) |
| Urinary Sodium (mmol/d) | 186 ± 42 (p = 0.03) | 125 ± 13 (p = 0.043) | 160 ± 12 (p = 0.024) |

Values are expressed as mean ± SD

Figure 2:
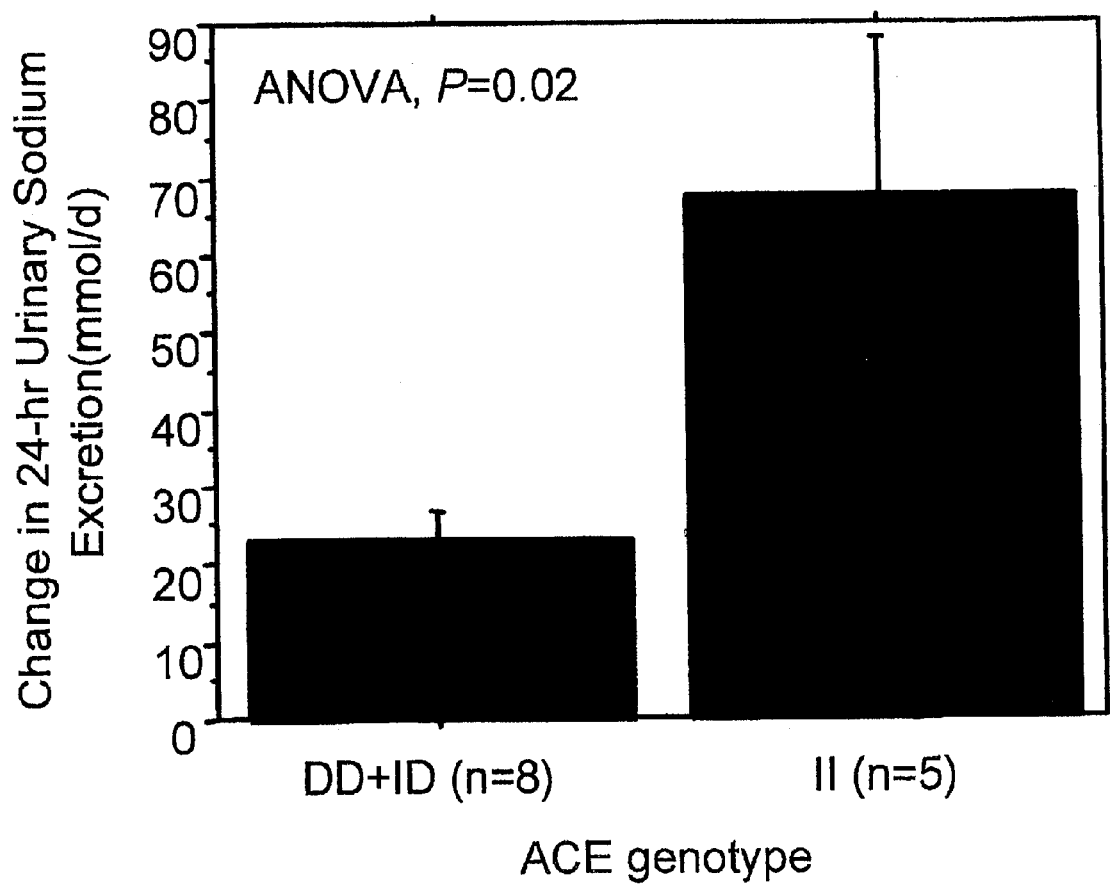
FIG. 2 shows the change in sodium excretion levels of the same thirteen subjects, grouped by either having or not having a "D" allele.

The increase in sodium excretion in response to limited exercise training tended to be higher in the "II" genotype group (57% increase) compared to the "ID" (23% increase) and "DD" (16% increase) genotype groups (p=0.079). FIG. 1 shows the "before and after" results in graph form. FIG. 2 shows the change in sodium excretion levels in the subjects grouped by either having or not having a "D" allele.

Example 2

Variations in Increase of Sodium Excretion in Thirty (30) Subjects After Limited Exercise The study of Example 1 was increased to a total of thirty male and female African American subjects, aged 51±8years, obese (body fat>35%), sedentary (VO$_2$max21.8±4.8 ml/kg/min) and hypertensive (BP 145±4 over 90±3 mmHg). The insertion/deletion ACE gene ("II" n=8; "ID" n=10; "DD" n=12) polymorphism was determined using standard PCR procedures.

Exercise consisted of 7 consecutive days of treadmill walking and stationary cycling for 50 min/d at 65% of heart rate reserve. Sodium excretion was determined by 24-hour urine collection at baseline and beginning 14–18 hours after the last exercise session. Subjects consumed diets identical in macronutrient and sodium content during the testing periods. Baseline sodium excretion, fasting insulin and glucose levels, percent body fat, VO$_2$max, and casual mean blood pressure (MBP) were similar in the ACE genotype groups.

After seven days of exercise training, sodium excretion was significantly increased in all three genotype groups, as shown in Table 3:

TABLE 3

| | ACE Genotype | | |
|---|---|---|---|
| | II (n = 5) | ID (n = 4) | DD (n = 4) |
| Urinary Sodium (before) (mmol/d) | 119 ± 26 | 110 ± 16 | 138 ± 11 |
| Urinary Sodium (after) (mmol/d) | 166 ± 42 | 130 ± 13 | 160 ± 12 |
| P value | 0.04 | 0.04 | 0.02 |

Values are expressed as mean ± SD

The increase in sodium excretion tended to be higher in the "II" genotype group (39% increase) compared to the "ID" (18% increase) and "DD" (16% increase) genotype groups (p=0.06).

We claim:

1. A method of increasing sodium excretion levels in a hypertensive human subject, the method comprising:

identifying a hypertensive human subject having a II genotype for human angiotensin converting enzyme gene (ACE), wherein the human subject is in need of increased sodium excretion levels;

engaging the human subject in limited exercise training for a period of time sufficient to increase sodium excretion levels in the human subject; and testing the sodium excretion levels of the human subject following the period of time sufficient to increase sodium excretion levels, wherein said engaging results in an increase in sodium excretion levels in the hypertensive human subject.

* * * * *